United States Patent [19]

Plaue et al.

[11] Patent Number: 5,545,718
[45] Date of Patent: Aug. 13, 1996

[54] SYNTHETIC PEPTIDES OF THE CONJUGATE OF UBIQUITINE AND H2A HISTONE

[75] Inventors: Serge Plaue, Haguenau; Sylviane Muller; Marc Van Regenmortel, both of Strasbourg, all of France

[73] Assignee: Pasteur Sanofi Diagnostics, Marnes la Coquette, France

[21] Appl. No.: 418,435

[22] Filed: Apr. 7, 1995

Related U.S. Application Data

[62] Division of Ser. No. 655,437, filed as PCT/FR90/00280 Apr. 23, 1990, Pat. No. 5,427,958.

[30] Foreign Application Priority Data

Apr. 26, 1989 [FR] France ................ 89 05531

[51] Int. Cl.$^6$ .............. C07K 5/00; C07K 7/00; C07K 17/00; C07K 16/00
[52] U.S. Cl. ............. 530/327; 530/328; 530/387.9; 530/388.1; 530/388.85; 530/389.1
[58] Field of Search ................ 530/327, 328, 530/387.9, 388.1, 388.85, 389.1

[56] References Cited

PUBLICATIONS

Goldknopf et al, PNAS, vol. 74 pp. 864–868 1977.
Ericsson et al Exp. Cell Res. vol. 167 pp. 127–134 1986.
Throne et al EMBO Journal vol. 6, pp. 1005–1010 1987.
Muller et al PNAS, vol. 85 pp. 8176–8180 1988.
Harlow et al "Antibodies, A Laboratory Manual" Cold Spring Harbor Laborabory pp. 128–129 1988.
Kohler et al Nature vol. 256 pp. 495–497 1975.
Thanavala et al J. Exp. Med. vol. 164 pp. 227–236 1986.
Muller et al J. Exp. Med. pp. 1607–1617 1989.

Primary Examiner—Toni R. Scheiner
Assistant Examiner—Sheela J. Huff
Attorney, Agent, or Firm—Jacobson, Price, Holman & Stern, PLLC

[57] ABSTRACT

Peptides possessing some of the immunological properties of the peptide of the formula Gly-Gly-Arg-Leu; Lys-Lys-Thr-Glu. Application to the diagnosis of certain autoimmune diseases and to the vaccine.

5 Claims, No Drawings

SYNTHETIC PEPTIDES OF THE CONJUGATE OF UBIQUITINE AND H2A HISTONE

This is a divisional of application Ser. No. 07/655,437, filed as PCT/FR90/00280 Apr. 23, 1990, now U.S. Pat. No. 5,427,958.

The object of the present invention is peptides that can be recognized by antibodies in biological fluids, in particular serums in patients or animals stricken with auto-immune diseases such as Disseminated Lupus Erythematosus or diseases of the nervous systems such as Alzheimer's or Parkinson's diseases.

The invention also concerns applications of these peptides and compositions containing them in in vitro diagnoses in man of the potentiality of certain auto-immune or nervous-system diseases, as well as their use in diagnostic kits.

The invention further concerns the application of these peptides in the production of immunogenic compositions and of vaccines used against these diseases.

Finally, the invention concerns antibodies that can be induced in vivo by these immunogenic peptides and compositions which contain them used for in vitro diagnosis in patients stricken with auto-immune or nervous-system diseases, as well as the manufacture of medications used against these diseases.

Stress proteins are involved in a variety of diseases, such as non-viral infections and certain auto-immune diseases. Thus, S. Muller et al. (*Proc. Natl. Acad. Sci.*, USA 85:8176, 1988) have described ubiquitine, a thermal-shock protein containing 76 amino acid residues which is present in all eukaryote cells as a principal antigenic target of Disseminated Lupus Erythematosus. V. Manetto et al. have shown (*Proc. Natl. Acad. Sci.*, USA 85:4501, 1988), that ubiquitine is implicated in diseases of the nervous system, such as Alzheimer's and Parkinson's diseases. B. S. Polla (*Immunol. Today*, 9:134, 1988) has demonstrated that thermal shock proteins may play a central role in all cases of inflammation in which a rise in temperature is a significant clinical sign.

It is accepted today that ubiquitine may be present in cells both in the free state and united with a large number of proteins of the nucleus, the cytoplasm, or the membrane, or may also be linked to the network of microtubules.

The conjugates of ubiquitine of the cytosol are known to be selective mediators of the breakdown of damaged or abnormal proteins.

In the nucleus, the role of the conjugates of ubiquitine with the H2A and H2B histones remains poorly understood. The formation of these conjugates is a product of a selective, reversible histone modification, which occurs most notably in the actively transcribed areas of the chromatin and which may be involved in the relaxation of the chromatin. Ubiquitine may also indirectly modulate the structure of the chromatin, by stimulating the activity of the deacetylase histone enzyme. An article by M. Rechsteiner (*Ann. Rev. Cell. Biol.*, 3:1 1987) states that conjugates of ubiquitine with the histones of the nucleus break down more slowly than those of ubiquitine of the cytosol.

H. Busch et al. (*Molec. Cell. biol.*, 3:1, 1981) and A. W. Thorne et al. (*EMBO J.*, 6:1005, 1987) have described the fact that, in the nucleus, ubiquitine is enzymatically conjugated with histones by means of a peptide bond between the group α-COOH of the C-terminal glycine in position 76 of the ubiquitine and the group—NH2 of the lateral lysine chain in position 119 in the H2A histone and in position 120 in the H2B histone, thus forming branched molecules.

In mammal cells, the H2A and H2B histones conjugated with ubiquitine are present in the proportions of 10% and 1%, respectively.

S. Muller et al. have described (*Proc. Natl. Acad. Sci.*, USA 85:8176, 1988) the presence, in serums of patients stricken with Disseminated Lupus Erythematosus, of antibodies capable of reacting in an immuno-enzymatic ELISA-type test with ubiquitine and with a synthetic fragment corresponding to the residues of amino acids 22 to 45 of said ubiquitine.

More extensive studies have enabled the Applicant to conclude that, in immuno-transfer blot techniques, the serums of patients suffering from Disseminated Lupus Erythematosus also react with two polypeptides having atomic mass numbers of approximately 52 and 43 kilodaltons and identified, surprisingly, as contaminants in a commercial ubiquitine preparation.

By using an antiserum specific for the H2A and H2B histones, the Applicant has shown that these two polypeptides having an atomic mass number of 43 and 2 kilodaltons corresponded, respectively, to the ubiquitine conjugated with the H2A histone and to a mixture of ubiquitine conjugated with the H2A and the H2B histone.

The work carried out on the peptide sequence of the ubiquitine and of the conjugates of ubiquitine with the histones has led inventors to prepare synthetic peptides corresponding to the branched part of the conjugate of ubiquitine with the H2A histone. This work has enabled them to confirm the presence of the conjugate of the ubiquitine with the H2A histone in polypeptides having atomic mass numbers of 43 and 53 kilodaltons.

Antiserums of animals immunized with these peptides react specifically with the conjugate of the ubiquitine and of the H2A histone, and not with the H2A histone and/or with the free ubiquitine. Furthermore, the serums of patients stricken with Disseminated Lupus Erythematosus reacting immunologically with the ubiquitine also react with these peptides.

These peptides are thus applicable to the diagnosis of Disseminated Lupus Erythematosus and more broadly, to all autoimmune or nervous system diseases in which the conjugate of ubiquitine with the H2A histone plays a role.

The research conducted on these peptides has demonstrated their immunogenic importance or capability of being made immunogenic, in order to induce in vivo the production of antibodies which can recognize the conjugate of ubiquitine with the H2A histone. This conjugate appears to play an important role in the appearance of auto-antibodies in Disseminated Lupus Erythematosus, thus indicating strongly the use of these peptides for the preparation of a vaccine against this type of disease.

To designate below the amino acid residues which are constituents of the peptides according to the invention, the following description makes use of a three-letter nomenclature for each natural amino acid, as follows:

Ala Alanine Cys cysteine Asp aspartic acid Glu glutamic acid Phe phenylalanine Gly glycine His histidine Ile isoleucine Lys lysine Leu leucine Met methionline Pro proline Ser serine Thr threonine Val valine Trp tryptophane Tyr tyrosine.

The peptides according to the invention have immunological properties in common with the peptide corresponding to the following formula:

The peptides preferred according to the invention have the following formula:

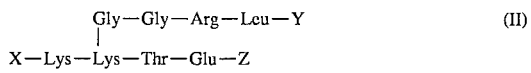

in which:

X and Y represent either an NH2 group which is free or in which amide is introduced by one or two alkyl groups comprising from 1 to 5 carbon atoms, or a peptide group containing from 1 to 10 amino acid residues, in which the N-terminal amino acid has a free or amide-containing NH2 group, as before.

Z represents either a free or alkoxyl OH group which then contains an alkyl group comprising 1–5 carbon atoms, or a peptide group containing 1–10 amino acid residues, in which the C-terminal amino acid had a free or alkoxyl OH group, as before.

The groups comprising 1–10 amino acid resides contained in X and/or Y and/or Z are selected essentially so as to preserve the immunological properties of the peptide corresponding to formula (I).

In formula (I), the sequence Gly-Gly-Arg-Leu corresponds to the fraction of the ubiquitine sequence, and the Lys-Lys-Thr-Glu sequence corresponds to the fraction of the H2A histone sequence at the branching point between these two compounds in the conjugate of the ubiquitine with the H2A histone. Thus, the groups containing 1–10 amino acid residues contained in X and/or Y and/or Z may, in particular, correspond to the adjoining amino acids of the peptide corresponding to formula (I) in the ubiquitine-H2A histone conjugate.

Among the formula (II) peptides, preference is given to those in which:

Y represents either a free NH2 group or a Tyr residue containing a free NH2 group; X represents a Cys residue whose amine function can possibly be acetylated; and Z represents an OH group.

Among the formula (II) peptides, preference is given to those in which:

Y represents either a free NH2 group or a Tyr residue containing a free NH2 group; X represents the linking of the two Leu and Pro residues, the Pro residue being linked by a peptide bond to the adjacent Lys residue of X in formula (II) and the amine function of the Leu residue being possibly acetylated; and Z represents an OH group.

The invention specifically focuses on peptides corresponding to the following formulae:

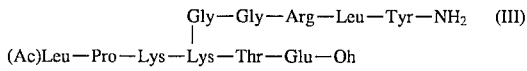

in which the amine function of the Leu residue is acetylated (AC); and

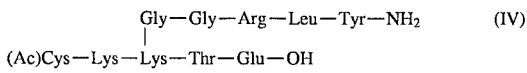

in which the amine function of the Cys residue is acetylated (Ac).

In addition to the above-mentioned peptides, the invention concerns peptides which are modified by the insertion and/or deletion and/or substitution of one or several amino acids, as long as the antigenic or immunogenic properties of said peptides are not modified, as well as those in which the peptide bond (—C—NH—) is replaced, for example, by the following structures: —CO—N(CH3)—, —CH2Ch2—, —CO—CH2—, or again, in which the peptide skeleton has one or several inserted groups such as the groups —CH2—, —NH—, or —O—. The present invention also encompasses peptides in which the amino acid residues having an asymmetrical carbon are in the form of D or L.

The peptides according to the invention may be prepared using conventional techniques involving peptide synthesis in the solid phase, either by the successive condensation of the amino acid residues in the required order, or by condensation of the amino acid residues on a previously-formed fragment which contains several amino acids in the suitable order, or, yet again, by condensation of several previously-prepared fragments, taking care to preliminarily protect all of the reactive functions borne by the amino acid residues or fragments, except for the amine and carboxyl functions involved in the peptide bond formed during condensation.

According to one example of the preparation of a peptide according to the invention, the Glu residue, whose amine function is protected by a terbutyloxycarbonyl group, is fixed on a resin by means of its carboxylic group. Next, after removing the protection of the amine function by washing the resin with trifluoroacetic acid in dichloromethane, the second amino acid residue, whose amine function is protected as specified above, is linked in dimethylformamide. Thus, the amino acid residues are fixed one after the other, these residues forming the portion of the peptide according to the invention which corresponds to the fraction of the H2A histone sequence. After the removal of the protection, the amine function of the N-terminal residue can be acetylated under the effect of an excess of acetic anhydride in the presence of diisopropylethylamine.

The lateral chains of the trifunctional amino acids must be protected, for example by using the following groups: cyclohexyl for glutamic acid, benzyl for threonine, tosyl for arginine, paramethylbenzyl for cysteine, 2,6-dichlorobenzyl for tyrosine, fluorenylmethyloxycarbronyl for one of the lysines and 2-chlorobenzyloxycarbonyl for the other lysine.

The lateral chain of the lysine on which branching occurs is advantageously protected by a fluorenymethoxycarbonyl group. After removal of protection of the lysine using a mixture of piperidine and dimethylformamide, the first glycine residue corresponding to the fraction of the ubiquitine sequence is linked as before. Using this residue as a base, the amino acids which will form the peptide chain are gradually linked on the amine group whose protection is preliminarliy removed on each occasion, the portion already formed remaining attached to the resin.

After having removed all protective groups, the peptide according to the invention is removed from the solid substrate, for example using hydrofluoric acid. The raw product is lyophilized and undergoes chromatography in the liquid phase under medium pressure, thus making it possible to obtain a product whose purity reaches approximately 93%. This latter is then characterized by using chromatography in the liquid phase under high pressure and by analyzing its amino acid composition and by mass spectrometry.

Analysis of the amino acid composition of the peptides corresponding to formulae (III) and (IV) gives the following results (expected values are given in parentheses):

peptide corresponding to formula (III):

Glx 1.00 (2); Gly 2.00 (2); Arg 0.95 (1); Thr 1.15 (1); Pro 0.95 (1); Tyr 1.02 (1); Leu 1.82 (2); Lys 2.11 (2)

peptide corresponding to formula (IV):

Glx 1.01 (1); Gly 1.97 (2); Arg 0.97 (1); Thr 1.08 (1); Tyr 1.03 (1); Cys 0.87 (1); Leu 1.06 (1); Lys 1.87 (2).

The molar mass of the peptides corresponding to formulae (II) and (III), as confirmed by mass spectrometry using the FAB method, are the following (the computed values appear in parentheses):

peptide (III): 1303.8 (1303.5)

peptide (IV): 1196.6 (1196.6).

The stability of the peptides corresponding to the formulae (III) and (IV) was verified using HPLC analysis. No deterioration was found after several months of storage at ambient temperature and in the dark, dimerization of the peptide corresponding to formula (VI) is less than 9%, because of its terminal Cys residue.

The invention also concerns the conjugates obtained by linking peptides according to the invention to carrier molecules which may be physiologically acceptable and non-toxic.

Thus, the peptides corresponding to formula (II), in which Y represents a Tyr residue, may advantageously be linked to a carrier protein using bis-diazobenzidine. According to another embodiment of the invention, the peptides corresponding to formula (II) in which X represents a Cys residue may be linked to a carrier molecule or to a substrate by means of a thiol group.

As carrier molecules, natural proteins such as tetanic formol toxoid, albumin, or serum albumins may be mentioned.

The peptides according to the invention possess antigenic properties and may thus be used in diagnostic procedures for determining, or in the follow-up of patients stricken with, autoimmune or nervous system diseases in which the ubiquitine-H2A histone conjugate is involved. The invention further concerns a composition containing at least one of the peptides liable to be recognized by the antibodies in the serum or any other biological fluid of patients suffering from these diseases. The in vitro detection of the peptide-antibody complex is performed by means of immuno-enzymatic ELISA-type, immunofluorescence, radio-immunological, or radio-immunoprecipitation tests.

To perform these tests, the invention also concerns the peptides according to the invention marked using a suitable marker, for example biotin or its derivatives, an enzyme like peroxidase, a fluorescent marker like fluorescein, a radioactive marker such as a radioisotope, etc.

These tests include, for example, the following steps:

deposit of a predetermined quantity of a composition containing a peptide or a conjugate of a peptide according to the invention, in the wells of a titration microplate or on another substrate such as balls;

deposits of the biological fluid to be tested in the wells or incubation of the fluid with the balls;

after incubation or washing of the microplates or balls, deposit in the wells or incubation with the balls of a system for the detection of the peptide-antibody complex possibly formed.

The immuno-enzymatic ELISA-type tests performed on serums of patients stricken with Disseminated Lupus Erythematosus have demonstrated that 96% of a given population of serums which recognize ubiquitine react with the peptides corresponding to formula (IV); conversely, only 13% of serums not reacting with ubiquitine possess antibodies capable of binding the formula (IV) peptide. Out of the group of patients stricken with Disseminated Lupus Erythematosus, 51.8% of serums contain antibodies against the H2A histone, and 53.8% of these react with the formula (IV) peptide, as against 46.1% which do not react.

The invention further concerns antibodies formed against peptides according to the invention. These antibodies may be polyconal or monoclonal, and are thus produced by any hibridoma prepared according to conventional methods for producing cellular fusion between the splenic cells of an animal immunized against any of the invention peptides and cells from a line of myeloma cells.

Rabbit antiserums have been prepared based on the formula (IV) peptide linked to ovalbumin. The antibodies obtained react with neither ubiquitine nor the H2A histone during immuno-enzymatic ELISA-type tests. Using immunotransfer techniques, these antibodies have made it possible to show that contaminating fractions having atomic mass numbers of 43 and 52 kilodaltons corresponded to ubiquitine-H2A histone conjugates.

Because of the very special branched structure of the invention peptides, the antibodies prepared using these peptides constitute very specific probes of the ubiquitine-H2A histone conjugates which are incapable of binding free ubiquitine or H2A histone.

While it proved impossible until now to distinguish free ubiquitine from ubiquitine conjugated with the H2A histone, the antibodies according to the invention make it possible to identify the conjugate unequivocally.

Furthermore, the antibodies formed against the invention peptides and the auto-antibodies of patients which react with said peptides and obtained after affinity chromatography can be used to prepare anti-idiotype antibodies partially forming an exact copy of the initial antigenic peptide, and which are, therefore, capable of bonding with the auto-antibodies observed in auto-immune diseases.

The present invention also concerns these anti-idiotype antibodies and compositions containing them, as well as their application in the in vitro diagnosis in man of the presence of auto-antibodies and the production of medications used to combat these auto-immune diseases.

The invention also concerns immunogenic compositions used to produce vaccines whose active agent is formed by at least one peptide or one anti-idiotype antibody according to the invention which, possibly linked to a carrier molecule, leads to the production of antibodies against said peptides and which are capable of interfering with the pathology and/or clinical manifestations of the auto-immune diseases. The pharmaceutical compositions according to the invention, which may be used as vaccines, are made up of solutions or suspension which can be injected or administered by other means and can be administered in doses of between 10 μg/kg and 100 mg/kg of peptides according to the invention.

We claim:

1. A peptide having the formula

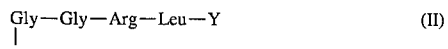

$$\begin{array}{c} \text{Gly}-\text{Gly}-\text{Arg}-\text{Leu}-\text{Y} \\ | \\ \text{X}-\text{Lys}-\text{Lys}-\text{Thr}-\text{Glu}-\text{Z} \end{array} \quad (\text{II})$$

wherein X is $NH_2$, Cys, or Leu-Pro—, wherein $NH_2$ moieties are optionally substituted with hydrogen, $C_{1-5}$ alkyl, acetyl, Y is $NH_2$, or Tyr, wherein $NH_2$ moieties are optionally substituted with $C_{1-5}$ alkyl or acetyl, and Z is OH, or $C_{1-5}$ alkoxy.

2. A peptide having the formula
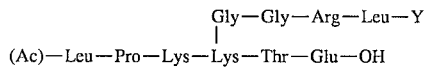
wherein Y is NH₂ or Tyr-NH₂.
3. A peptide having the formula
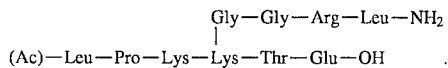
4. A peptide having the formula
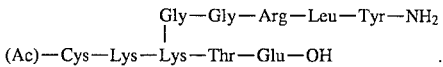
5. A monoclonal or polyclonal antibody prepared from the peptide of claim 1 that has a binding affinity for ubiquitine histone conjugate without binding to ubiquitine alone or H₂A alone.
\* \* \* \* \*